United States Patent [19]

Jackson et al.

[11] Patent Number: 5,212,092
[45] Date of Patent: May 18, 1993

[54] STORAGE AND CALIBRATION SOLUTION FOR MULTIPARAMETER INTRAVASCULAR BLOOD GAS SENSOR DEVICE

[75] Inventors: Jeffrey T. Jackson, Poway; Henry K. Hui, Laguna Niguel, both of Calif.

[73] Assignee: Puritan-Bennett Corporation, Carlsbad, Calif.

[21] Appl. No.: 887,679

[22] Filed: May 22, 1992

[51] Int. Cl.⁵ ............... G01N 31/00; G01C 17/38; A61B 5/05
[52] U.S. Cl. ................. 436/11; 436/18; 436/127; 436/133; 73/1 R; 73/23.21; 204/403
[58] Field of Search ............. 436/8, 11, 18, 133, 436/127; 73/1 R, 23.21; 204/403

[56] References Cited

U.S. PATENT DOCUMENTS

| | | | |
|---|---|---|---|
| 3,824,157 | 7/1974 | Macur | 204/1 T |
| 3,884,640 | 5/1975 | Lock et al. | 23/230 R |
| 4,469,562 | 9/1984 | Chang | 204/1 T |
| 4,469,792 | 9/1984 | Simmonds et al. | 436/11 |
| 4,485,174 | 11/1984 | Chang et al. | 436/11 |
| 4,567,748 | 2/1986 | Klass et al. | 73/1 G |
| 4,689,308 | 8/1987 | Gerhard | 436/18 |
| 4,722,904 | 2/1988 | Feil | 436/11 |
| 5,045,529 | 9/1991 | Chiang | 514/6 |

OTHER PUBLICATIONS

Otto S. Wolfbeis and Leonie J. Weis, *Fiber-Optic Fluorosensor for Oxygen and Carbon Dioxide*, 1988, pp. 2028-2030, vol. 60, Anal. Chem.

Primary Examiner—James C. Housel
Assistant Examiner—N. Bhat
Attorney, Agent, or Firm—Fulwider Patton Lee & Utecht

[57] ABSTRACT

The solution for storage and calibration of an intravascular blood sensor is an aqueous solution of from 10-35 mM of a first buffer component of bicarbonate, and at least one additional buffer component selected to maintain the pH of the solution substantially at or slightly below a neutral pH, and preferably below approximately pH 8. The first and additional buffering components preferably are selected to act in two separate pH regions with substantially no overlap of the buffering capacity of the different buffering components, and the concentration of the first buffer component in the solution is selected to permit a two point calibration of the intravascular multiparameter blood sensor by carbon dioxide and oxygen gas tonometry.

11 Claims, No Drawings

STORAGE AND CALIBRATION SOLUTION FOR MULTIPARAMETER INTRAVASCULAR BLOOD GAS SENSOR DEVICE

BACKGROUND OF THE INVENTION

1. Field of the Invention

This invention relates generally to chemical and biochemical analysis of an analyte in a fluid or gaseous mixture, and more particularly concerns a composition for a solution for storage and calibration of an intravascular or intra-arterial multiparameter blood gas sensor incorporating at least a pH sensing element and a carbon dioxide sensing element.

2. Description of Related Art

Measurement of acidity (pH) and the tension or partial pressure of carbon dioxide and oxygen in the blood is important in modern medicine for determination of the respiratory condition of a patient. Multiparameter sensors for taking intravascular measurements of acidity, carbon dioxide and oxygen levels in the blood have been developed in which a fluorescent indicator dye is encapsulated within a membrane cover such as a hydrophobic or hydrophilic matrix which is permeable to the analyte to be measured, coupled to one or more optical fibers for measuring the intensity of fluorescence of the indicator dye. The fluorescence intensity of appropriately chosen indicators is altered according to the level of acidity, carbon dioxide, or oxygen being measured, allowing measurement of blood levels of these parameters through a compatible intravascular catheter system.

Aqueous solutions of bicarbonate are commonly useful for calibration of pH sensors, or multiparameter sensors including pH, $O_2$ and $CO_2$ sensing elements by gas tonometry, by infusion of carbon dioxide gas into a calibration solution in the tonometer. One prior art reference, for example, discloses isotonic saline solutions containing 1.52 grams per liter of sodium bicarbonate, equilibrated with 10.02% carbon dioxide in nitrogen, or containing 1.9108 grams per liter of sodium bicarbonate equilibrated with 4.80% carbon dioxide, 11.62% oxygen, and the balance nitrogen, for calibration of a pH sensor. Another reference discloses a buffer solution containing 0.01 molar sodium bicarbonate and 1.0 molar sodium chloride, for calibration of a carbon dioxide sensor. A 15 mM bicarbonate buffer solution for calibration of an oxygen and carbon dioxide combination sensor is also known.

Solutions of two or more buffer components are also known. However, such conventional multicomponent buffer solutions typically are designed to cover a broad pH range, and work additively to maintain a desired pH range. These solutions are generally not useful for calibration by gas tonometry.

Calibration of multiparameter pH, $CO_2$ and $O_2$ blood gas sensors typically involves tonometry with two different gas compositions containing different gas levels in a calibration solution. The concentrations of both carbon dioxide and oxygen are typically selected to be changed in the gas compositions to bracket the physiological normal levels of these gases in the blood. It would also theoretically be desirable to formulate the calibration solution so that the two different carbon dioxide levels in the two selected gas compositions would result in two different pH levels in the normal physiological range bracketing the normal physiological pH of 7.4. However, this has been found in practice to necessitate formulation of a buffer solution with an initial pH at ambient atmospheric carbon dioxide levels much higher than the physiological normal value, usually greater than a pH of 8.5. Storage of an intravascular multiple parameter sensor in a solution with such a high pH can have deleterious effects on the surface of the multiple sensor which comes in contact with blood, resulting in reduced blood compatibility, especially when a silicone polymer forms a principal part of the surface of the intravascular sensor.

It has also been found that in the process of steam sterilization of intravascular blood gas and pH sensors stored in a buffered calibration solution, the calibration solution can become highly alkaline, often reaching a pH of 9 or more. Under such conditions of high temperature and pH, the surface of the intravascular device which comes into contact with blood can also be chemically altered, and such chemical alterations can also lead to blood compatibility problems. It has also been found that when multiparameter pH, $CO_2$ and $C_2$ sensors are stored in such a solution which has been exposed to steam sterilization, such high pH levels can further cause the carbon dioxide sensing element to experience drift of measurements of carbon dioxide. In view of these problems, it would be desirable to provide a solution for storage and calibration of such intravascular blood sensors that is buffered to maintain a pH substantially at or slightly below a near neutral pH, and preferably less than pH 8, in the absence of $CO_2$ gas in the solution after exposure to the elevated temperatures of steam especially during sterilization.

For calibration of a multiparameter blood gas and pH sensor incorporating a carbon dioxide sensing element, it would be desirable to provide an improved calibration solution in which the sensor can also be stored to maintain a substantially neutral pH without interference with or loss of the gas tonometric properties of the solution. The present invention meets these needs.

SUMMARY OF THE INVENTION

Briefly, and in general terms, the present invention provides for a solution for storage and calibration of an intravascular multiparameter blood sensor, in which the solution is buffered to maintain the pH of the solution at or slightly below near neutral, during and following steam sterilization without loss of the gas tonometric properties of the solution.

The invention accordingly provides for a storage and calibration solution comprising an aqueous solution of from 10-35 mM of a first buffer component selected from the group consisting of bicarbonate and carbonate salts; and at least one additional buffer component selected to maintain the pH of the solution at or below a near neutral pH, which is preferably below pH 8, even in the substantial absence of $CO_2$ gas in the solution. The first and additional buffering components preferably are selected to act in two separate pH regions with substantially no overlap of the buffering capacity of the different buffering components, and the concentration of the first buffer component in the solution is selected to permit a two point calibration of the pH, $CO_2$ and $O_2$ sensing elements of the intravascular multiparameter blood sensor in a physiologically significant range by carbon dioxide and oxygen gas tonometry. The additional buffer component selected is preferably selected to maintain the pH of the solution at or below approximately neutral pH of 7.5 at an initial atmospheric carbon dioxide level, and even under conditions of high temperature and substantial absence of $CO_2$ gas. The additional buffer component most preferably maintains the pH of the solution between 7.0 and 8.0, even under conditions of high temperature and substantial absence of $CO_2$ gas. The additional buffer component is preferably selected from one or more of the following: 3[(1,1-Dimethyl-2-hydroxyethyl)amino]-2-hydroxypropanesulfonic acid and salts thereof, N,N-bis[2-Hydroxyethyl]glycine, boric acid and salts thereof, and N-tris[Hydroxymethyl]methyl-3-aminopropanesulfonic acid and salts thereof. In addition, the osmolarity of the storage and calibration solution is preferably set to be comparable to the osmolarity of blood or other vascular tissues where the sensor is to be used.

The invention further provides for a method for calibrating a multiparameter intravascular blood sensor in such a storage and calibration solution buffered to maintain the neutral pH of the solution without loss of the gas tonometric properties of the solution following steam sterilization of the solution. In the method of the invention, the intra-vascular blood sensor is placed in the solution, and the blood sensor is sterilized in the buffer solution with high temperature steam. The solution is then infused with a first composition of mixed calibration gases, usually containing initial desired concentrations of carbon dioxide and oxygen, and a first measurement of a parameter related to the first concentration of one of the calibration gases in the first gas composition is performed. The solution is then infused with a second composition of the calibration gases, and a second measurement of a parameter related to the second concentration of the same calibration gas in the gas composition is performed, for a two point calibration of the sensor.

These and other aspects and advantages of the invention will become apparent from the following detailed description.

DETAILED DESCRIPTION OF THE PREFERRED EMBODIMENTS

During steam sterilization of intravascular multiparameter blood gas and pH sensors, the storage solution can become highly alkaline, often reaching a pH of 9 or more. This alkalinity can cause blood compatibility problems and drift of measurements from a carbon dioxide sensing element in the sensor due to high pH levels. For storage and calibration of such a multiparameter blood gas and pH sensor, a solution containing about 10-35 mM bicarbonate is needed for calibration of a pH sensing element. The solution must also maintain a substantially neutral pH during and following the high temperatures of steam sterilization even under conditions of substantial absence of $CO_2$ gas, and at temperatures typically ranging approximately from 10° C. to 130° C., and the buffer system must not interfere with the gas tonometric properties of the solution, for calibration of pH, $CO_2$ and $O_2$ sensing elements in the intravascular multiparameter sensor.

The invention accordingly provides for an aqueous solution for storage and calibration of an intravascular or intra-arterial multiparameter blood sensor, containing at least two buffering agents which act in two separate pH regions with no or minimal overlap of the buffering capacity of the different buffering components to maintain the pH of the solution under conditions of high temperature and substantial absence of $CO_2$ gas approximately equal to or slightly below near neutral pH, and preferably below pH 8. In comparison with conventional buffering agents, it is important that the buffering agents of the invention should not alter or significantly decrease the accuracy and increase the time needed to perform a two point gas tonometric calibration, and that the buffering agents permit a two point gas tonometric calibration with different gas compositions containing different concentrations or partial pressures of either oxygen or carbon dioxide gas in a physiologically significant range.

The storage and calibration solution of the invention is preferably isotonic, isoionic, and isoosmotic with blood, and is preferably an aqueous solution containing 10-35 mM concentration of a first buffering agent of bicarbonate, such as cesium bicarbonate ($CsHCO_3$), potassium bicarbonate ($KHCO_3$), or sodium bicarbonate ($NaHCO_3$), or other similar bicarbonate salts. Alternatively, cesium carbonate ($Cs_2CO_3$), potassium carbonate ($K_2CO_3$), or sodium carbonate ($Na_2CO_3$), or similar salts, can also be used for forming the bicarbonate buffering concentration of the first buffering agent, as the equilibrium of carbonate and bicarbonate ions is well known.

The solution preferably also includes at least one additional buffer component to maintain pH of the solution at or near neutral pH without interference or loss of the gas tonometric properties of the solution following steam sterilization of the solution. The additional buffer component is preferably selected from the group consisting of the following buffer agents: 3[(1,1-Dimethyl-2-hydroxyethyl)amino]-2-hydroxypropanesulfonic acid (AMPSO) and salts thereof; N,N-bis[2-Hydroxyethyl]glycine (BICINE) and salts thereof; boric acid, or borate salts; and N-tris[Hydroxymethyl]methyl-3-aminopropanesulfonic acid (TAPS) and salts thereof. Most preferably, the additional buffer agents are provided in concentrations of from about 20-100 mM AMPSO, 20-100 mM BICINE, from about 20-100 mM boric acid or borate, and 20-100 mM TAPS in the solution.

The osmolarity of the solution is preferably adjusted to the osmolarity of the vascular environment where the probe is used. For example, for an intravascular placement, the osmolarity of the solution should be in the range of from about 285 to about 320 mosm. The osmolarity can be adjusted to the desired level by adding to the solution a salt such as sodium chloride, potassium chloride, or other similar salts such as salts of strong acids, and combinations thereof.

In the method of the invention of calibrating an intravascular or intra-arterial blood sensor such as a multiparameter blood sensor in the above described storage and calibration solution, the blood sensor is preferably placed in a storage container in which the sensor can also be calibrated by tonometry, containing the buffer solution with at least two buffer components as described above. The method of the invention is also particularly advantageous in maintaining blood compatibility of a sensor having a silicone polymeric material that forms a principal part of the blood contacting surface of the intravascular sensor, as discussed above. The blood sensor is sterilized in the buffer solution in the container by subjecting the solution and blood sensor in the container to high temperature steam at a temperature of from 121° C.–135° C. Thereafter, the blood sensor can be stored in the solution in the container until the blood sensor is to be used, at which time the blood sensor can be calibrated in the solution in the container, by performing a two point gas calibration in a physiologically significant range. Calibration of multiparameter blood gas sensors typically involves tonometry at two different gas levels in a calibration solution. Where the gases to be measured are carbon dioxide and oxygen, the concentrations of these gases are typically selected to bracket the physiological normal levels. The physiologically significant range of carbon dioxide concentration, for example, is typically from 2 weight percent to 15 weight percent carbon dioxide, with the balance of the gas being inert gas. In terms of partial pressures, in the case of carbon dioxide, the normal partial pressure ($pCO_2$) to be bracketed is 40 mmHG, and for oxygen, the normal partial pressure ($pO_2$) to be bracketed is 100 mmHG. The buffer solution of the present invention provides for an initial approximately neutral pH of about or slightly below 7.5 at ambient atmospheric $CO_2$ concentrations. In the method of the invention, when this buffer solution is exposed to concentrations of $CO_2$ which bracket the physiological normal $pCO_2$ level, pH levels are produced in the solution which bracket the normal physiological pH of 7.4, and allow for accurate blood pH measurements. Experiments in humans and baboons have shown that the storage and calibration of intravascular multiparameter blood sensors in such buffer solutions maintaining a pH between 7.0 and 8.0 greatly improve the blood compatibility of the sensors. Thus, in the method of the invention, the solution is infused with a gas composition containing first concentrations of a calibration gases within the physiological ranges, such as a mixture of oxygen and carbon dioxide, typically with the remainder of the gas composition being inert gas such as nitrogen, and a first measurement of a parameter related to the first concentration of gas is performed with the sensor, to obtain a first point of the calibration. The solution is then infused with a second gas composition containing different concentrations of the calibration gases within the physiological ranges, and a second measurement of a parameter related to the second concentration of the calibration gas is performed, to obtain the second point in the calibration.

In experiments in which a multiparameter blood sensor was stored and steam sterilized in the solutions described, the pH of the solution also remained substantially at or slightly below an approximately neutral pH following steam sterilization. In two point tonometric calibration of the sensor with mixed calibration gases of carbon dioxide and oxygen, carried out in the steam sterilized solutions, the calibrations were found to be accurate, reliable, and timely.

It should therefore be evident in light of the above that the storage and calibration solution of the invention can be used for storing and calibrating an intravascular blood sensor while maintaining a pH substantially at or slightly below a near neutral pH, preferably lower than pH 8, and that the buffering compositions of the solution of the invention maintain this pH level despite exposure to steam sterilization, loss of $CO_2$ gas, and without loss of the gas tonometric properties of the solution.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A method for calibrating an intravascular blood sensor in a solution for storage and calibration of an intravascular multiparameter blood sensor buffered to maintain the pH of the solution without loss of the gas tonometric properties of the solution following steam sterilization of the solution, the solution comprising an aqueous solution of from 10–35 mM of a first buffer component selected from the group consisting of bicarbonate and carbonate salts and at least one additional buffer component selected to maintain the pH of the solution at or below a pH of approximately 8, the steps of the method comprising:
    placing the intra-vascular blood sensor in said solution;
    sterilizing the blood sensor in the buffer solution with high temperature steam;
    infusing the solution with a first concentration of a calibration gas;
    performing a first measurement of a parameter related to said first concentration of said calibration gas;
    infusing the solution with a second concentration of said calibration gas; and
    performing a second measurement of a parameter related to said second concentration of said gas.

2. The method of claim 1, wherein said gas is carbon dioxide.

3. The method of claim 1, wherein said gas is oxygen.

4. The method of claim 1, further including the step of adjusting the osmolarity of the solution to be in the range of from about 285 mosm to about 320 mosm.

5. The method of claim 1, wherein said additional buffer component is selected from one or more of the compounds in the group consisting of 3[(1,1-Dimethyl-2-hydroxyethyl)amino]-2-hydroxypropanesulfonic acid and salts thereof, N,N-bis[2-Hydroxyethyl]glycine, boric acid and salts thereof, and N-tris[Hydroxymethyl]methyl-3-aminopropanesulfonic acid and salts thereof.

6. A method for calibrating an intravascular blood sensor in a solution for storage and calibration of an intravascular multiparameter blood sensor buffered to maintain the pH of the solution without loss of the gas tonometric properties of the solution following steam sterilization of the solution, the solution comprising an aqueous solution of from 10–35 mM of a first buffer component selected from the group consisting of bicarbonate and carbonate salts and at least one additional buffer component selected to maintain the pH of the solution at or below approximately neutral pH, said first and additional buffering components acting in two separate pH regions with substantially no overlap of the buffering capacity of the different buffering components, the steps of the method comprising:
    placing the intra-vascular blood sensor in said solution;
    sterilizing the blood sensor in the buffer solution with high temperature steam;
    infusing the solution with a first gas composition containing a first concentration of a calibration gas;
    performing a first measurement of a parameter related to said first concentration of said calibration gas;
    infusing the solution with a second gas composition containing a second concentration of said calibration gas; and
    performing a second measurement of a parameter related to said second concentration of said gas.

7. The method of claim 6, wherein said gas is carbon dioxide.

8. The method of claim 6, wherein said gas is oxygen.

9. The method of claim 6, wherein said additional buffer component is selected from one or more of the compounds in the group consisting of 3[(1,1-Dimethyl-2-hydroxyethyl)amino]-2-hydroxypropanesulfonic acid and salts thereof, N,N-bis[2-Hydroxyethyl]glycine, boric acid and salts thereof, and N-tris[Hydroxymethyl]methyl-3-aminopropanesulfonic acid and salts thereof.

10. The method of claim 6, wherein said intravascular blood sensor includes an exterior surface adapted to come into contact with blood, and a principal portion of said surface is formed from a silicone polymer.

11. The method of claim 6, further including the step of adjusting the osmolarity of said solution to be in the range of about 285 mosm to about 320 mosm by the addition of a salt selected from the group consisting of sodium chloride, potassium chloride, salts of strong acids, and combinations thereof.

* * * * *